United States Patent [19]
Hansenne et al.

[11] Patent Number: 5,985,250
[45] Date of Patent: Nov. 16, 1999

[54] STABILISED SUNSCREEN COMPOSITIONS

[75] Inventors: Isabelle Hansenne; Martin Josso, both of Paris, France

[73] Assignee: Societe L'oreal S.A., Paris, France

[21] Appl. No.: 09/091,005

[22] PCT Filed: Dec. 5, 1996

[86] PCT No.: PCT/FR96/01945

§ 371 Date: Aug. 24, 1998

§ 102(e) Date: Aug. 24, 1998

[87] PCT Pub. No.: WO97/21422

PCT Pub. Date: Jun. 19, 1997

[30] Foreign Application Priority Data

Dec. 8, 1995 [FR] France ................... 95/14579

[51] Int. Cl.⁶ ................ A61K 7/42; A61K 7/44; A61K 7/00
[52] U.S. Cl. ................ 424/59; 424/60; 424/400; 424/401
[58] Field of Search ................ 424/59, 60, 400, 424/401

[56] References Cited

FOREIGN PATENT DOCUMENTS

| 94 04131 | 3/1994 | European Pat. Off. . |
| 0 685 225 | 6/1995 | European Pat. Off. . |
| 0 685 228 | 6/1995 | European Pat. Off. . |
| 0 678 292 | 10/1995 | European Pat. Off. . |

*Primary Examiner*—Shelley A. Dodson
*Attorney, Agent, or Firm*—Burns, Doane, Swecker & Mathis, L.L.P.

[57] ABSTRACT

The present invention relates to the use of 2-ethylhexyl α-cyano-β,β-diphenylacrylate in, or for the manufacture of, cosmetic compositions containing p-methylbenzylidenecamphor in combination with at least one dibenzoylmethane derivative, for the purpose of improving the stability of p-methylbenzylidenecamphor in such compositions.

8 Claims, No Drawings

STABILISED SUNSCREEN COMPOSITIONS

The present invention relates to the use of 2-ethylhexyl α-cyano-β,β-diphenylacrylate in, or for the manufacture of, cosmetic compositions containing p-methylbenzylidenecamphor in combination with at least one dibenzoylmethane derivative, for the purpose of improving the stability of p-methylbenzylidenecamphor in such compositions.

It is known that light radiation with wavelengths of between 280 nm and 400 nm allow tanning of the human epidermis and that rays with wavelengths of between 280 nm and 320 nm, which are known as UV-B rays, cause skin burns and erythema which hinder the development of a natural tan; this UV-B radiation should thus be screened out.

It is also known that UV-A rays, with wavelengths of between 320 nm and 400 nm, which cause tanning of the skin, are liable to bring about an adverse change therein, in particular in the case of sensitive skin or skin continually exposed to solar radiation. UV-A rays in particular cause a loss of elasticity of the skin and the appearance of wrinkles, leading to premature ageing. They promote triggering of the erythemal reaction or amplify this reaction in certain individuals and may even be the cause of phototoxic or photoallergic reactions. It is thus desirable also to screen out UV-A radiation.

In this respect, dibenzoylmethane derivatives, and most particularly 4-tert-butyl-4'-methoxydibenzoylmrethane, sold under the trade name "Parsol 1789" by the company Givaudan, are particularly advantageous UV-A screening agents given their high intrinsic power of absorption. However, these screening agents have the drawback of being photoreactive, i.e. they degrade under the action of light and thus lose their photoprotective properties towards the skin and the hair.

The Applicant has already proposed, in patent application FR-2,607,700, to combine p-methylbenzylidenecamphor with 4-tert-butyl-4'-methoxydibenzoylmethane in order to improve the light-stability of cosmetic compositions containing 4-tert-butyl-4'-methoxydibenzoylmethane.

However, this solution is not entirely satisfactory, given the fact that p-methylbenzylidenecamphor is itself subject to gradual disappearance under the action of light. In cosmetic compositions containing it, the concentration of p-methylbenzylidenecamphor falls under the action of light and they thus lose their photoprotective efficacy.

After considerable research conducted in the field of photoprotection mentioned above, the Applicant has now discovered that the introduction of 2-ethylhexyl α-cyano-β,β-diphenylacrylate into a composition containing p-methylbenzylidenecamphor in combination with at least one dibenzoylmethane derivative, and in particular with 4-tert-butyl-4'-methoxydibenzoylmethane, makes it possible to significantly improve the stability of the p-methylbenzylidenecamphor in such compositions, and thus the overall efficacy of these compositions.

This discovery forms the basis of the invention.

The subject of the present invention is thus the use of 2-ethylhexyl α-cyano-β,β-diphenylacrylate in, or for the manufacture of, cosmetic compositions comprising p-methylbenzylidenecamphor and a dibenzoylmethane derivative, in particular 4-tert-butyl-4'-methoxyodibenzoylmethane, in order to improve the stability of p-methylbenzylidenecamphor in the said compositions.

The subject of the invention is also a process for improving the stability, and thus the efficacy, of a cosmetic composition comprising p-methylbenzylidenecamphor and a dibenzoylmethane derivative, in particular 4-tert-butyl-4'-methoxydibenzoylrnethane, the said process consisting in introducing into the said composition an effective amount of 2-ethylhexyl α-cyano-β,β-diphenylacrylate.

Thus, according to the present invention, cosmetic compositions containing at least one dibenzoylmethane derivative in combination with p-methylbenzylidenecamphor can be prepared, in which the concentration of p-methylbenzylidenecamphor remains relatively constant even if these compositions are subjected to the action of light.

Other characteristics, aspects and advantages of the present invention will become apparent on reading the detailed description which follows.

The compositions towards which the present invention is directed thus contain p-methylbenzylidenecamphor in combination with at least one dibenzoylmethane derivative.

As mentioned above, the dibenzoylmethane derivatives towards which the present invention is directed are products that are already well known per se and described in particular in the documents FR-A-2,326,405, FR-A-2,440,933 and EP-A-0,114,607, the teachings of which documents, as regards the aspects which relate to the actual definition of these products, are included in the present description in their entirety by way of references.

Among the dibenzoylmethane derivatives towards which the present invention is more particularly directed, mention may be made in particular, in a non-limiting manner, of:

2-mesthyldibenzoylmethane, 4-methyldibenzoylmethane, 4-isopropyldibenzoylmethane, 4-tert-butyldibenzoylmethane, 2,4-dimethyldibenzoylmethane, 2,5-dimethyldibenzoylmethane, 4,4'-diisopropyldibenzoylmethane, 4-ter-butyl-4'-methoxydibenzoylmethane, 2-methyl-5-isopropyl-4'-methoxydibenzoylmethane, 2-methyl-5-tert-butyl-4'-methcxydibenzoylmethane, 2,4-dimethyl-4'-methoxydibenzoylmethane, 2,6-dimethyl-4-tert-butyl-4'-methoxydibenzoylmethane.

Among the dibenzoylmethane derivatives mentioned above, it is most particularly preferred, according to the present invention, to use 4-tert-butyl-4'-methoxydibenzoylmethane, in particular that sold under the trade name "Parsol 17891" by the company Givaudan, this screening agent corresponding to the structural formula (I) below:

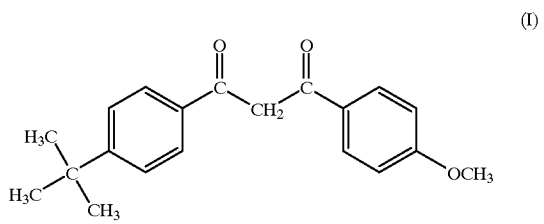

(I)

Another dibenzoylmethane derivative which is preferred according to the present invention is 4-isopropyldibenzoylmethane, this screening agent being sold under the name "Eusolex 8020" by the company Merck and corresponding to the structural formula (II) below:

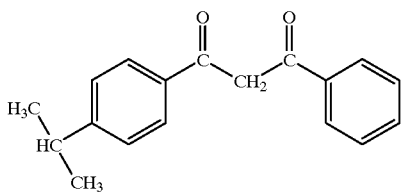

(II)

p-Methylbenzylidenecamphor is a liposoluble screening agent which is known per se, absorbing the UV-B range and sold in particular under the trade name "Eusolex 6300" by the company Merck.

2-Ethylhexyl α-cyano-β,β-diphenylacrylate, also known as octocrylene, is itself a liquid lipophilic screening agent which is already known per se for its activity in the UV-B range. It is a product which is commercially available, and is sold in particular under the name "Uvinul N 539" by the company BASF. It corresponds to formula (III) below:

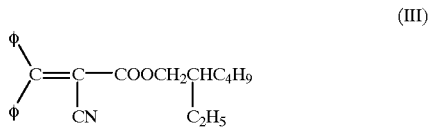

(III)

in which φ denotes a phenyl radical.

Thus, when 2-ethylhexyl α-cyano-β,β-diphenylacrylate is added in sufficient amount to a composition containing p-methylbenzylidenecamphor and a dibenzoylmethane derivative, in particular 4-tert-butyl-4'-methoxydibenzoylmethane, an increase in the light-stability of this composition, and thus an increase in its efficacy over time, are observed.

The 2-ethylhexyl α-cyano-β,β-diphenylacrylate is preferably present in the compositions according to the invention at a content at least equal to 0.5% by weight relative to the total weight of the composition. Even more preferably, this content is between 0.5% and 3% by weight relative to the total weight of the composition.

The cosmetic compositions towards which the present invention is directed can, needless to say, contain one or more hydrophilic or lipophilic complementary sunscreens which are active in the UVA and/or UVB range (absorbers) other than, of course, the three screening agents mentioned above. These complementary screening agents can be chosen in particular from c,innamic derivatives, salicylic derivatives, camphor derivatives other than p-methylbenzylidenecamphor, such as, for example, benzene-1,4-di(3-methylidene-10-camphorsulphonic acid), triazine derivatives, benzophenone derivatives, β,β-diphenylacrylate derivatives other than 2-ethylhexyl α-cyano-β,β-diphenylacrylate, p-aminobenzoic acid derivatives, and the screening polymers and screening silicones described in application WO 93/04665. Other examples of organic screening agents are given in patent application EP-A-0,487,404.

The compositions according to the invention can also contain agents for artificially browning and/or tanning the skin (self-tanning agents), such as, for example, dihydroxyacetone (DHA).

The cosmetic compositions according to the invention can also contain pigments or nanopigments (average primary particle size: generally between 5 nm and 100 nm, preferably between 10 and 50 nm) of coated or uncoated metal oxides such as, for example, nanopigments of titanium oxide (amorphous or crystallized in rutile and/or anatase form), of iron oxide, of zinc oxide, of zirconium oxide or of cerium oxide, which are all photoprotective agents that are well known per se, which act by physically blocking (reflecting and/or scattering) the UV radiation. Standard coating agents are, moreover, alumina and/or aluminium stearate. Such coated or uncoated metal oxide nanopigments are described in particular in patent applications EP-A-0,518,772 and EP-A-0,518,773.

The compositions in accordance with the present invention can also comprise standard cosmetic adjuvants chosen in particular from fatty substances, organic solvents, ionic or nonionic thickeners, softeners, antiox.idants, opacifiers, stabilizers, emollients, silicones, α-hydroxy acids, antifoaming agents, moisturizers, vitamins, fragrances, preserving agents, surfactants, fillers, sequestering agents, polymers, propellants, basifying or acidifying agents, dyes or any other ingredient usually used in cosmetics, in particular for the manufacture of antisun compositions in the form of emulsions.

Needless to say, a person skilled in the art will take care to select the optional complementary compound(s) mentioned above and/or the amounts thereof such that the advantageous properties intrinsically associated with the ternary combination in accordance with the invention are not, or are not substantially, adversely effected by the addition(s) envisaged.

The fatty substances can consist of an oil or a wax or mixtures thereof, and they also comprise fatty acids, fatty alcohols and fatty acid esters. The oils can be chosen from animal, plant, mineral or synthetic oils and in particular from liquid petroleum jelly, liquid paraffin, volatile or nonvolatile silicone oils, isoparaffiris, poly-α-olefins, fluoro oils and perfluoro oils. Similarly, the waxes can be chosen from animal, fossil, plant, mineral or synthetic waxes that are known per se.

Among the organic solvents, mention may be made of lower alcohols and polyols.

The thickeners can be chosen in particular from crosslinked polyacrylic acids and modified or unmodified guar gums and cellulose gums, such as hydroxypropyl guar gum, methylhydroxyethylcellulose and hydroxypropylmethylcellulose.

The compositions according to the invention can be prepared according to techniques which are well known to those skilled in the art, in particular those techniques intended for the preparation of oil-in-water or water-in-oil type emulsions.

This composition can in particular be in the form of a simple or complex (O/W, W/O, O/W/O or W/O/W) emulsion such as a cream, a milk, a gel, a cream-gel, a powder or a solid tube and can optionally be packaged as an aerosol and can be in the form of a mousse or a spray.

When it is an emulsion, the aqueous phase of this emulsion can comprise a nonionic vesicle dispersion prepared according to known processes (Bangham, Standish and Watkins. J. Mol. Biol. 13, 238 (1965), FR 2,315,991 and FR 2,416,008).

The cosmetic composition of the invention can be used as a composition for protecting the human epidermis or the hair against ultraviolet rays, as an antisun composition or as a make-up product.

When the cosmetic composition according to the invention is used for protecting the human epidermis against UV rays, or as an antisun composition, it can be in the form of a suspension or a dispersion in solvents or fatty substances, in the form of a nonionic vesicle dispersion or alternatively in the form of an emulsion, preferably of oil-in-water type, such as a cream or a milk, or in the form of an ointment, a gel, a cream-gel, a solid tube, a stick, an aerosol mousse or a spray.

When the cosmetic composition according to the invention is used for protecting the hair, it can be in the form of a shampoo, a lotion, a gel, an emulsion, a nonionic vesicle dispersion or a lacquer for the hair and can constitute, for example, a rinseout composition, to be applied before or after shampooing, before or after dyeing or bleaching, before, during or after permanent-waving or straightening the hair, a styling or treating lotion or gel, a blow-drying or hairsetting lotion or gel or a composition for permanent-waving, straightening, dyeing or bleaching the hair.

When the composition is used as a make-up product for the eyelashes, the eyebrows or the skin, such as a skin treatment cream, a foundation, a tube of lipstick, an eyeshadow, a blusher, a mascara or an eye liner, it can be in solid or pasty, anhydrous or aqueous form, such as oil-in-water or water-in-oil emulsions, nonionic vesicle dispersions or alternatively suspensions.

As a guide, for the antisun formulations in accordance with the invention which have a vehicle of oil-in-water emulsion type, the aqueous phase (in particular comprising the hydrophilic screening agents) generally represents from 50 to 95% by weight, preferably from 70 to 90% by weight, relative to the formulation as a whole, the oily phase (in particular comprising the lipophilic screening agents) generally represents from 5 to 50% by weight, preferably from 10 to 30% by weight, relative to the formulation as a whole, and the (co)emulsifier(s) generally represent(s) from 0.5 to 20% by weight, preferably from 2 to 10% by weight, relative to the formulation as a whole.

A concrete, but in no way limiting, example illustrating the invention will now be given.

EXAMPLE

| Six oil-in-water emulsions of the following composition were prepared: | |
|---|---|
| p-Methylbenzylidenecamphor (Eusolex 6300) | 4.5% |
| 4-tert-Butyl-4'-methoxydibenzoylmethane (Parsol 1789) | 1.5% |
| 2-Ethylhexyl α-cyano-β,β-diphenylacrylate (Uvinul N 539) | X% |
| Glyceryl monostearate/PEG stearate (100 EO) mixture sold under the trade name "Arlacel 165" by the company ICI | 1.5% |
| Pure double-distilled cetyl alcohol (90% C16) | 1.7% |
| Crosslinked polyacrylic acid | 0.2% |
| C12/C15 alkyl benzoate | 8% |
| Potassium hexadecyl phosphate | 1% |
| Triethanolamine | 0.2% |
| Ethylenediaminetetraacetic acid, disodium salt, 2H$_2$O | 0.1% |
| Cyclomethicone sold under the name "DC 245 Fluid" by the company Dow Corning | 5% |
| α,ω-dihydroxy polydimethylsiloxane/cyclotetra- and cyclopentadimethylsiloxane mixture (56/44) (14/86) | 5% |
| Antioxidant | 0.5% |
| Moisturizers | 15% |
| Preserving agents | qs |
| Sterilized demineralized water | qs 100.0% | with X being varied from 0 to 10%.

For each of these emulsions, the percentage of residual p-methylbenzylidenecamphor after irradiation by UV according to the following procedure was determined: for each formula, four control samples and four test samples were prepared. 16 mg of formula were placed on frosted PMMA (polymethyl methacrylate) plates, which had been prerinsed with water and then dried, and the formula was spread over an area of 2×4 cm$^2$. The plates were then all left to stand in the darkness for half an hour. Next, the plates were irradiated (Suntest CPS Heraeus) for 4 hours and 5 minutes, while keeping the control plates in darkness during the irradiation time of the other plates.

The samples were then assayed in the following way: the screening agents were extracted by immersing each plate in 50 g of isopropanol in order to dissolve the screening agents. The plates and the solvent containing the screening agents were then treated with ultrasound for 5 minutes in order to ensure efficient agitation. The total concentration of residual UV-B screening agent (Uvinul N 539+Eusolex 6300) was assayed by spectrophotometer.

Since the 2-ethylhexyl α-cyano-β,β-diphenylacrylate itself is entirely photostable (no significant degradation), the initial concentration of 2-ethylhexyl α-cyano-β,β-diphenylacrylate was removed from this total concentration of UV-B screening agent: the concentration of residual p-methylbenzylidenecamphor (Eusolex 6300) was thus obtained.

The concentration of residual UV-A screening agent (Parsol 1789) was also measured.

The results, as a percentage of residual screening agent, are given in Table (I) below:

TABLE I

| % of Uvinul N 539 added | % of residual Eusolex 6300 (UV-B screening agent) | % of residual Parsol 1789 (UV-A screening agent) |
|---|---|---|
| 0% | 65% | 62% |
| 0.5% | 84% | 78% |
| 1.5% | 76% | 74% |
| 3% | 88% | 87% |
| 6% | 79% | 87% |
| 10% | 88% | 92% |

These results show clearly that the presence of 2-ethylhexyl α-cyano-β,β-diphenylacrylate (Uvinul N 539) in a composition containing p-methylbenzylidenecamphor (Eusolex 6300) in combination with 4-tert-butyl-4'-methoxydibenzoylmethane (Parsol 1789) increases the stability of the p-methylbenzylidenecamphor. Once 0.5% 2-ethylhexyl α-cyano-β,β-diphenylacrylate is added to a composition containing 4.5% p-methylbenzylidenecamphor and 1.5% 4-tert-butyl-4'-methoxydibenzoylmethane, the stability of the p-methylbenzylidenecamphor is improved significantly. Given that the p-methylbenzylidenecamphor photostabilizes the 4-tert-butyl-4'-methoxydibenzoylmethane (cf. FR-2,607,700), it is consequently observed (column 3 of Table (I)) that the photostability of the 4-tert-butyl-4'-methoxydibenzoylmethane is itself markedly improved.

The composition according to the invention is thus particularly photostable overall.

We claim:

1. A method to improve the stability of p-methylbenzylidenecamphor in a cosmetic composition comprising p-methylbenzylidene camphor and a dibenzoylmethane derivative, said method comprising introducing an effective amount of 2-ethylhexyl α-cyano-β,β-diphenylacrylate to said composition to improve the stability of p-methylbenzylidenecamphor.

2. The method according to claim 1, wherein said dibenzoylmethane derivative is 4-tert-butyl-4'-methoxydibenzoylmethane.

3. The method according to claim 1, wherein said dibenzoylmethane derivative is 4-isopropyldibenzoylmethane.

4. The method according to claim 1, wherein said 2-ethylhexyl α-cyano-β,β-diphenylacrylate is present in said composition at a content at least equal to 0.5% by weight relative to the total weight of the composition.

5. The method according to claim 4, wherein said content is between 0.5% and 3% by weight relative to the total weight of the composition.

6. A process for improving the stability of cosmetic compositions comprising p-methylbenzylidenecamphor and a dibenzoylmethane derivative, said process comprising introducing into said compositions an effective amount of 2-ethylhexyl α-cyano-β,β-diphenylacrylate to improve the stability of the composition.

7. Process according to claim 6, wherein the dibenzoylmethane derivative is 4-tert-butyl-4'-methoxydibenzoylmethane.

8. Process according to claim 6, wherein the dibenzoylmethane derivative is 4-isopropyldibenzoylmethane.

* * * * *